US008895273B2

(12) United States Patent
Boer et al.

(10) Patent No.: US 8,895,273 B2
(45) Date of Patent: Nov. 25, 2014

(54) CONVERSION OF HEXURONIC ACID TO HEXARIC ACID

(75) Inventors: Harry Boer, Espoo (NL); Satu Hildich, Espoo (FI); Peter Richard, Espoo (FI); Merja Penttila, Espoo (FI)

(73) Assignee: Teknologian Tutkimuskeskus VTT, Espoo (FI)

( * ) Notice: Subject to any disclaimer, the term of this patent is extended or adjusted under 35 U.S.C. 154(b) by 338 days.

(21) Appl. No.: 13/141,736

(22) PCT Filed: Dec. 22, 2009

(86) PCT No.: PCT/FI2009/051029
§ 371 (c)(1),
(2), (4) Date: Sep. 13, 2011

(87) PCT Pub. No.: WO2010/072902
PCT Pub. Date: Jul. 1, 2010

(65) Prior Publication Data
US 2012/0045804 A1    Feb. 23, 2012

(30) Foreign Application Priority Data
Dec. 23, 2008 (FI) ................................ 2008 6236

(51) Int. Cl.
| C12P 21/00 | (2006.01) |
| C12P 7/44 | (2006.01) |
| C12N 9/00 | (2006.01) |
| C12N 1/00 | (2006.01) |
| C07H 21/04 | (2006.01) |
| C12N 9/04 | (2006.01) |

(52) U.S. Cl.
CPC ............... *C12P 7/44* (2013.01); *C12N 9/0006* (2013.01)
USPC ..... 435/142; 435/69.1; 435/183; 435/254.11; 536/23.2

(58) Field of Classification Search
None
See application file for complete search history.

(56) References Cited

U.S. PATENT DOCUMENTS 5,643,758 A * 7/1997 Guan et al. ................... 435/69.7

FOREIGN PATENT DOCUMENTS

| FI | WO 2006 128965 | 12/2006 |
| WO | WO 2009/145838 A2 | 12/2009 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession Q7CRQ0. Jul. 5, 2004.*
Accession Q888H1. Jun. 1, 2003.*
Whisstock et al. Q Rev Biophys. Aug. 2003;36(3):307-40.*
Moon, T.S. et al Production of Glucaric Acid from a Synthetic Pathway in Recombinant *Escherichia coli*. Applied and Environmental Microbiology, Feb. 2009, vol. 75, No. 3, p. 589-595. Published ahead of print on Dec. 5, 2008.
Database EMBL online,; Jan. 16, 2008; *Pseudomonas syringae* pv. tomato sir DC3000 uronate dehydrogenase (udh) gene, complete cds'. XP002575767 retrieved from EBI Accession No. EU377538.
Yoon, SH., et al "Cloning and Characterization of Uronate DeHydrogenases from Two *Pseudomonads* and *Agrobacterium tumefaciens* Strain C58". Journal of Bacteriology, Mar. 2009, vol. 191, No. 5, p. 1565-1573. Published ahead of print on Dec. 5, 2008, koko julkaisu.
Moon, TS, et al "Engineering microbial production of glucuronic and glucaric acids." Abstracts of Papers, 236th ACS National Meeting, Philadelphia, PA, Aug. 17-21, 2008, BIOT-929 Publisher: American Chemical Society, Washington, D.C. CODEN: 69KXQ2.
Zajic, JE "Hexuronic dehydrogenase of *Agrobacterium tumefaciens*" Journal of Bacteriology, 1959, vol. 78, p. 734-735.
Bateman, DF, et al "Purification and properties of uronate dehydrogenase from *Pseudomonas syringe*" Archives of Biochemistry and Biophysics, 1970, vol. 136, p. 97-105.
Database EMBL Online; Feb. 19, 2009, "TPA: *Agrobacterium tumefaciens* str. C58 uronate dehydrogenase (udh) gene, complete cds." XP002575766 retrieved from EBL accession No. EMBL:BK006462.
Antonius J A Van Maris, et al "Alcoholic fermentation of carbon sources in biomass hydrolysates by *Saccharomyces cerevisiae:* current status" Antonie Van Leeuwenhoek, Kluwer Academic Publishers, DO, vol. 90, No. 4; Oct. 11, 2006, pp. 391-418, XP019446684; ISSN:1572-9699 p. 405-407.
Richard Peter, etal "d-Galacturonic acid catabolism in microorganisms and its biotechnical relevance" Applied Microbiology and Biotechnology, vol. 82, No. 4, Mar. 2009, pp. 597-604, XP002575770; ISSN: 0175-7598.
Mojzita Dominik, et al; "Metabolic Engineering of Fungal Strains for Conversion of D-Galacturonate to meso-Galactarate"; Applied and Environmental Microbiology, vol. 76, No. 1; Nov. 6, 2009, pp. 169-175, XP008120892.
Boer, Harry, etal; "Identification in *Agrobacterium tumefaciens* of the D-galacturonic acid dehydrogenase gene." Applied Mircrobiology and Biotechnology; Apr. 2010; vol. 86, No. 3, Nov. 17, 2009, pp. 901-909, XP002575771, ISSN: 1432-0614.

* cited by examiner

*Primary Examiner* — Christian Fronda
(74) *Attorney, Agent, or Firm* — Gearhart Law, LLC

(57) ABSTRACT

The present invention relates to a method and microbial host strain for converting a hexuronic acid to a hexaric acid. In particular, the invention relates to the conversion of D-galacturonic acid to meso-galactaric acid (mucic acid). The invention also concerns an isolated nucleotide sequence. According to the present method a microbial host strain genetically modified to express uronate dehydrogenase enzyme (EC 1.1.1.203) is contacted with a biomaterial comprising hexuronic acid and the conversion products are recovered. By using the recombinant microorganisms of the present invention it is possible to treat biomaterials comprising hexuronic acids and thereby decrease the amount of hexuronic acids released to the environment.

23 Claims, 8 Drawing Sheets

ATGGCGATGAAACGGCTTCTTGTTACCGGTGCGGCGGGCCAGCTTGGCCGCGTCATGCGC
GAGCGTCTCGCACCGATGGCGGAGATACTGCGCCTTGCCGATCTCTCCCCGCTCGACCCG
GCAGGGCCGAACGAAGAATGCGTGCAATGCGACCTTGCCGATGCCAATGCCGTGAATGCC
ATGGTCGCCGGTTGCGACGGTATTGTTCATCTCGGCGGCATCTCGGTGGAGAAGCCCTTC
GAACAAATCCTTCAGGGCAATATCATCGGGCTTTATAATCTCTACGAGGCCGCCCGCGCC
CATGGACAGCCACGCATCGTCTTTGCCAGCTCCAACCACACGATCGGCTATTATCCGCAG
ACCGAACGGCTCGGTCCGGATGTTCCGGCGCGGCCGGACGGTCTTTACGGCGTCTCCAAA
TGTTTCGGCGAAAACCTCGCCCGCATGTATTTCGATAAATTCGGGCAGGAGACGGCGCTG
GTGCGCATCGGCTCCTGTACGCCGGAACCCAACAATTACCGCATGCTGTCCACCTGGTTT
TCGCACGATGATTTCGTGTCGCTGATCGAGGCGGTGTTTCGCGCGCCGGTGCTCGGCTGC
CCGGTCGTCTGGGGGGCATCGGCCAATGATGCGGGCTGGTGGGACAATTCGCATCTTGGC
TTTCTGGGCTGGAAACCGAAGGATAATGCCGAGGCCTTCCGGCGGCATATAACCGAGACG
ACACCGCCACCGGACCCGAATGACGCGTTGGTGCGGTTCCAGGGCGGTACGTTTGTCGAC
AACCCGATCTTCAAACAGAGC

Fig.3

MAMKRLLVTGAAGQLGRVMRERLAPMAEILRLADLSPLDPAGPNEECVQCDLADANAVNAMVAGCDGIVHLGGISVEKPFEQIL
QGNIIGLYNLYEAARAHGQPRIVFASSNHTIGYYPQTERLGPDVPARPDGLYGVSKCFGENLARMYFDKFGQETALVRIGSCTPE
PNNYRMLSTWFSHDDFVSLIEAVFRAPVLGCPVVWGASANDAGWWDNSHLGFLGWKPKDNAEAFRRHITETTPPPDPNDALV
RFQGGTFVDNPIFKQS

Fig. 4

```
CAAGGCCTAGGCGCGCCATGAGCTCGGATCCGGGCCCATGGCCTCCGCCCACACCACCCA
GACCCCCTTCAACCGCCTCCTCCTCACCGGCGCTGCTGGCGGCCTCGGCAAGGTCCTCCG
CGAAACCCTCCGCCCCTACTCCCACATCCTCCGCCTCTCCGATATCGCCGAGATGGCCCC
TGCCGTCGGCGATCACGAGGAAGTCCAGGTCTGCGATCTCGCCGATAAGGATGCCGTCCA
CCGCCTCGTCGAGGGCGTCGATGCCATCCTCCACTTCGGCGGTGTTAGCGTCGAGCGCCC
CTTCGAGGAAATCCTCGGCGCCAACATCTGCGGCGTGTTCCACATCTACGAGGCCGCTCG
CCGTCATGGTGTCAAGCGCGTCATCTTCGCCTCCAGCAACCACGTCATCGGCTTCTACAA
GCAGAACGAAACCATCGATGCCCACTCCCCACGCCGCCCTGATTCCTACTACGGCCTCTC
CAAGTCCTACGGCGAGGATATGGCCTCCTTCTACTTCGATCGCTACGGCATCGAAACCGT
GTCCATCCGCATCGGCTCCAGCTTCCCCGAGCCCCAGAACCGCCGCATGATGTCCACCTG
GCTGTCCTTCGATGATCTCACCCGCCTGCTCGAGCGCGCCCTCTACACCCCCGATGTCGG
CCACACCGTCGTCTACGGCGTGTCCGATAACAAGACCGTCTGGTGGGATAACCGATTCGC
TTCTAAGCTCGATTACGCCCCCAAGGATTCCTCCGAGGTGTTCCGCGCCAAGGTGGACGC
TCAGCCCATGCCTGCTGATGATGATCCTGCTATGGTCTACCAGGGTGGTGCCTTCGTCGC
CTCCGGCCCCTTCGGCGATAAGTAAACTAGTGGATCCGGTACCTCTTAATTAACTGGCCT
C
```

Fig. 9

MASAHTTQTPFNRLLLTGAAGGLGKVLRETLRPYSHILRLSDIAEMAPAVGDHEEVQ
VCDLADKDAVHRLVEGVDAILHFGGVSVERPFEEILGANICGVFHIYEAARRHGVKR
VIFASSNHVIGFYKQNETIDAHSPRRPDSYYGLSKSYGEDMASFYFDRYGIETVSIRIGS
SFPEPQNRRMMSTWLSFDDLTRLLERALYTPDVGHTVVYGVSDNKTVWWDNRFAS
KLDYAPKDSSEVFRAKVDAQPMPADDDPAMVYQGGAFVASGPFGDK

Fig. 10

CONVERSION OF HEXURONIC ACID TO HEXARIC ACID

FIELD OF THE INVENTION

The present invention relates to a method and microbial host strain for converting a hexuronic acid to a hexaric acid. In particular, the invention relates to the con-version of D-galacturonic acid to meso-galactaric acid (mucic acid).

DESCRIPTION OF RELATED ART

Biological waste material from industry including agriculture and pulp and paper industry contains sugars and their derivatives such as sugar acids. The conversion of such waste to useful products has been of interest and a challenge in the field of biotechnology for a long time. D-galacturonic acid is the major component of pectin, a low price raw material enriched e.g. in sugar beet pulp and citrus peel, and a carbon source for microorganisms living on decaying plant material. D-glucuronic acid and D-mannuronic acid are components for example in woody materials and algae.

There are at least three different pathways known for the catabolism of D-galacturonic acid (D-galacturonate):
1) The isomerase pathway that is present in e.g. *Escherichia coli*: This pathway consists of five enzymes converting D-galacturonate to pyruvate and D-glyceraldehyde-3-phosphate.
2) The oxidative pathway that is present in e.g. *Agrobacterium tumefaciens*: In this bacterial pathway D-galacturonic acid is first oxidized to meso-galactaric acid (mucic acid). This was described for *Pseudomonas* and for *Agrobacterium tumefaciens* (FIG. 1). An NAD dependent dehydrogenase is induced in *A. tumefaciens* cells growing on D-galacturonic acid. The enzyme has been partially purified and has shown activity with D-galacturonic and D-glucuronic acid (Chang and Feingold 1969).
3) The eukaryotic pathway that is present in *Aspergillus niger* and *Hypocrea jecorina* (FIG. 2) (earlier *Trichoderma reesei*): In the first step of this pathway D-galacturonic acid is reduced to L-galactonic acid by an NADPH utilizing reductase in *Hypocrea jecorina*, GAR1 (Kuorelahti et al. 2005 and WO2006/128965). The enzyme is reversible and specific for NADPH. In *Aspergillus niger* a D-galacturonic acid reductase, GAAA, was identified that could use NADPH and NADH, however NADPH had a higher affinity (Martens-Uzonova 2008). A gene ortholog of the *A. niger* gaaA exists also in *H. jecorina*, gar2, however according to Martens-Uzonova (2008) it is not known whether it is functional.

Sugar beet pulp and citrus fruit peel are currently dried and used as cattle feed. However, since drying is very energy consuming alternative uses for biomaterial comprising hexuronic acids, in particular D-galacturonic acid, would be desirable. Also in pulp and paper industry new treatment methods for side streams comprising sugars and sugar acids are needed.

As described above in the oxidative pathway D-galacturonic acid is oxidized to mucic acid in some bacteria. However, there are no reports that these bacteria could be used for the fermentation of D-galacturonic acid to mucic acid. The most likely reason for this is that the mucic acid is immediately metabolized further.

Mucic acid is currently a specialty chemical. It is made from galactose by oxidation with nitric acid. If produced at low price, it has the potential for a wider use. It is listed as one of the 30 most potential products produced from biomass listed in a study of the American NREL.

Since D-galacturonic acid is a cheap raw material, which is enriched in sugar beet pulp and citrus fruit peel, a method for catabolizing D-galacturonic acid (D-galacturonate) is needed. In particular, a cheap method for producing mucic acid is needed.

Furthermore, new methods for catabolizing other hexaric acids, such as D-glucuronic acid and mannuronic acid, are needed.

SUMMARY OF THE INVENTION

It is an aim of the present invention to provide novel methods and means for utilisation of biomaterials comprising sugars, sugar acids and their derivatives.

Another aim of the invention is to provide methods and means for degrading and utilising biomaterials comprising hexuronic acids.

A further aim of the present invention is provide a method for catabolizing D-galacturonic acid. In particular, an aim of the present invention is to provide a method for degrading biomaterial comprising D-galacturonic acid, such as pectin.

Still a further aim of the present invention is to provide a method for converting D-galacturonic acid to mucic acid.

One further aim of the invention is to provide a method for degrading and utilising biomaterial comprising D-glucuronic acid One further aim of the invention is to provide a method for degrading and utilising biomaterial comprising D-mannuronic acid.

Still a further aim of the present invention is to provide a method for converting D-glucuronic acid to D-glucaric acid and/or D-mannuronic acid to D-mannaric acid.

The present invention is based on the idea that a microbial host can be genetically modified to convert hexuronic acid to hexaric acid. This can be achieved by introducing a nucleotide sequence encoding uronate dehydrogenase enzyme (EC 1.1.1.203) into the host strain and express said nucleotide sequence in the host strain. A recombinant microbial strain can be used to degrade and utilise biomaterials comprising hexuronic acids.

According to one preferred embodiment of the invention the host is a eukaryotic host. Preferably the host is a fungus host, more preferably a filamentous fungus host.

Furthermore, according to another preferred embodiment of the invention a fungus host naturally consuming hexuronic acid, is genetically modified so that it can not consume it any more. The fungus host is genetically modified to produce uronate dehydrogenase enzyme (EC 1.1.1.203) and the host is capable of oxidizing hexuronic acid to hexaric acid. More specifically the fungus host is capable of converting D-galacturonic acid to mucic acid. The fungus host is also capable of converting D-glucuronic acid to D-glucaric acid and D-mannuronic acid to D-mannaric acid.

Currently mucic acid is made from galactose by oxidation with nitric acid. The new process would be a fermentation in which only air is utilised for the oxidation. The process would be cheaper, since no chemicals are used. Galacturonic acid is cheaper than galactose. With this method mucic acid can become a cheap bulk product.

By using the recombinant microorganisms of the present invention it is possible to treat biomaterials comprising hexuronic acids and thereby decrease the amount of hexuronic acids released to the environment.

Other objects, details and advantages of the present invention will become apparent from the following drawings, detailed description and examples.

BRIEF DESCRIPTION OF THE DRAWINGS

FIG. 3 shows the open reading frame of uro1 gene from *Agrobacterium tumefaciens* (SEQ ID NO: 3).

FIG. 4 shows the amino acid sequence encoded by uro1 gene (SEQ ID NO: 4).

FIG. 9 shows the nucleotide sequence encoding urinate dehydrogenase from *Pseudomonas* (SEQ ID NO: 19).

FIG. 10 shows the encoded amino acid sequence (SEQ ID NO: 20).

DETAILED DESCRIPTION OF THE PREFERRED EMBODIMENTS

Definitions

In connection with the present invention, the expression "uronate dehydrogenase enzyme" designates an enzyme classified as EC 1.1.1.203 by the enzyme classification.

D-galacturonic acid (D-galacturonate) is known to be catabolized through the following pathways:

1) Bacterial Pathway for D-Galacturonic Acid Catabolism:

The isomerase pathway that is present in e.g. *Escherichia coli*: This pathway consists of five enzymes converting D-galacturonate to pyruvate and D-glyceraldehyde-3-phosphate. The intermediate metabolites are D-tagaturonate, D-altronate, 3-Deoxy-D-erythro-hex-2-ulosonate and 3-Deoxy-D-erythro-hex-2-ulosonate-6-phosphate. The enzymes are uronate isomerase (EC 5.3.1.12), NADH-utilizing D-tagaturonate reductase (EC 1.1.1.5), altronate dehydratase (EC 4.2.1.7), 3-Deoxy-D-erythro-hex-2-ulosonate kinase (EC 2.7.1.45) and 3-Deoxy-D-erythro-hex-2-ulosonate-6-phosphate aldolase (EC 4.1.2.14).

Figure 1:
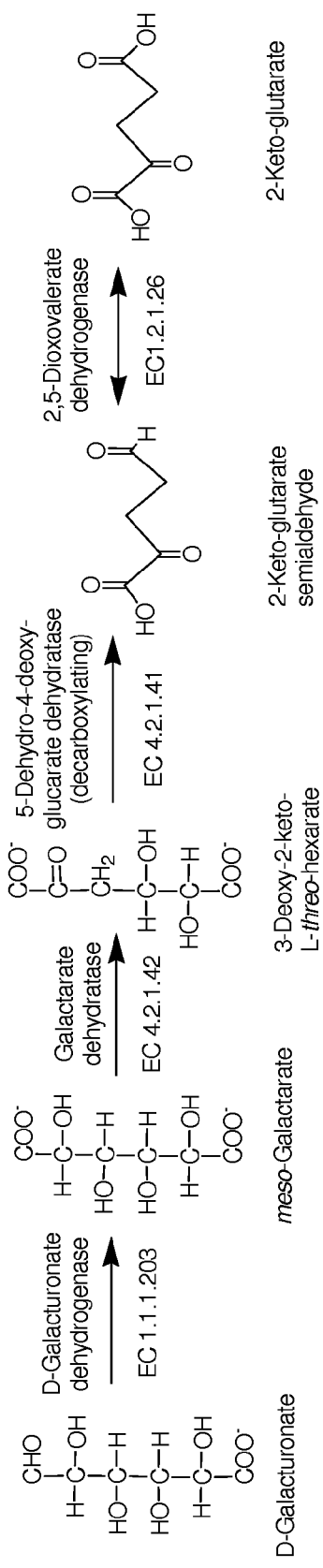
FIG. 1 shows the bacterial pathway for D-galacturonic acid catabolism. The first three metabolites are represented in Fischer projection. The C1 of the meso-galactarate (mucic acid) in this representation is the C6 of the 3-deoxy-2-keto-L-threo-hexarate. In this pathway the D-galacturonate dehydrogenase and the 2,5 dioxovalerate dehydrogenase are using NAD as a cofactor.

2) Oxidative Pathway for D-Galacturonic Acid Catabolism in Bacteria:

The oxidative pathway that is present in e.g. *Agrobacterium tumefaciens*: In this bacterial pathway D-galacturonic acid is first oxidized to meso-galactaric acid (mucic acid). This was described for *Pseudomonas* and for *Agrobacterium tumefaciens* (FIG. 1). An NAD dependent dehydrogenase is induced in *A. tumefaciens* cells growing on D-galacturonic acid. The partially purified enzyme showed activity with D-galacturonic and D-glucuronic acid (Chang and Feingold 1969). The immediate reaction product is probably a galactaric acid lactone (or D-glucaric acid lactone), which hydrolyses spontaneously. The hydrolysed reaction product is in general the more stable form; the reverse reaction of the D-galacturonate dehydrogenase is consequently not observed. The reverse reaction is only observed at acidic pH were galactaric acid lactone is present (Wagner and Hollmann 1976). meso-Galactaric acid (mucic acid) undergoes a dehydratation in the next step, and the reaction product is 3-Deoxy-2-keto-L-threo-hexaric acid (Chang and Feingold 1970).

The following steps involve a dehydratation and a decarboxylation and the reaction product is 2-ketoglutarate semialdehyde (2,5-dioxovalerate) (Chang and Feingold 1970). The dehydratation and decarboxylation is executed by a single enzyme (EC 4.2.1.41) which was described in more detail in *Pseudomonas acidovorans* (Jeffcoat 1975). 2-Ketoglutarate semialdehyde is subsequently oxidized to 2-ketoglutarate which is a metabolite in numerous pathways. Only the enzyme activities of these enzymes have been described. The corresponding genes have been identified in neither *A. tumefaciens* nor *P. acidovorans* or any other microorganism.

Figure 2:
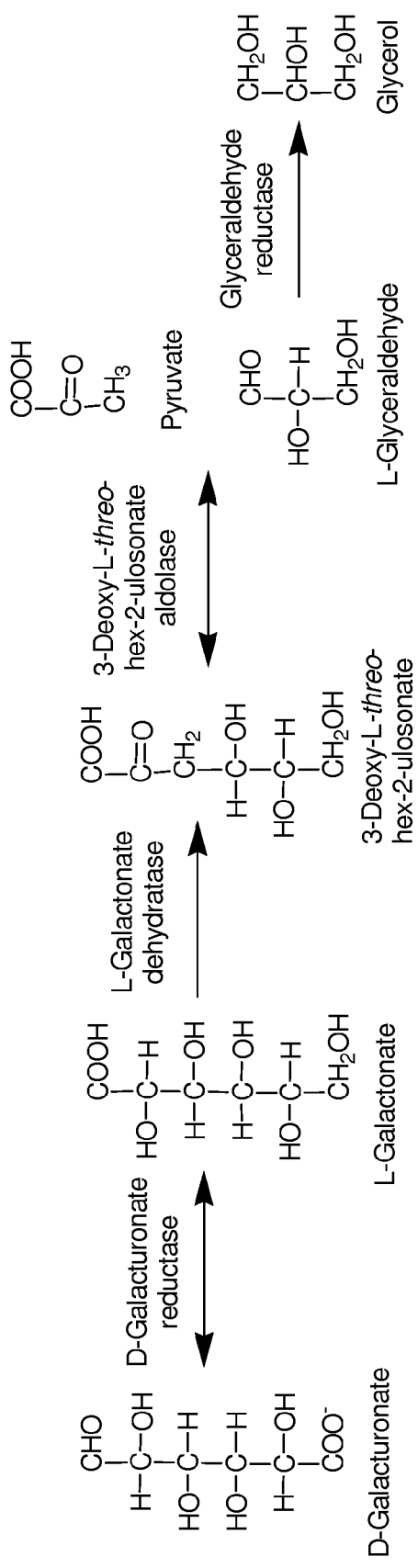
FIG. 2 shows the fungal pathway for D-galacturonic acid catabolism. The metabolites are represented in Fischer projection, which means that the C1 of the D-galacturonate becomes the C6 of the L-galactonate. The D-galacturonate reductase can be specific for their NADPH requirement or unspecific accepting NADH of NADPH depending on the organism.
Figure 5:
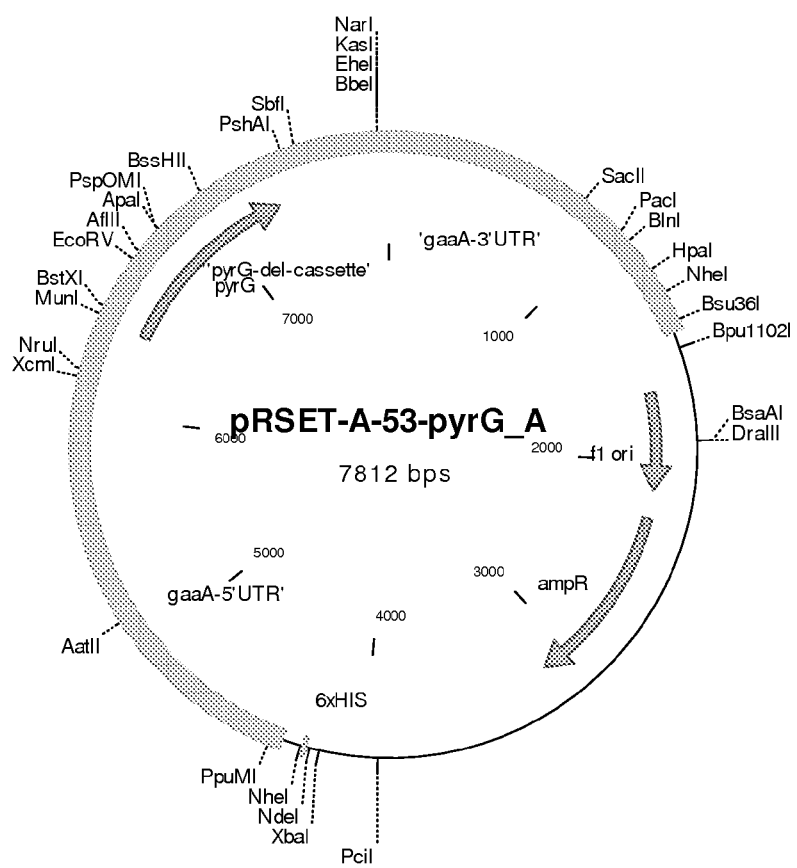
FIG. 5 shows the plasmid pRSET-A-53-pyrG_A

3) Eucaryotic Pathway for D-Galacturonic Acid Catabolism in Fungi:

The eukaryotic pathway that is present in *Aspergillus niger* and *Hypocrea jecorina* (FIG. 2): In the first step of this pathway D-galacturonic acid is reduced to L-galactonic acid by an NADPH utilizing reductase in *Hypocrea jecoria*, GAR1 (Kuorelahti et al. 2005 and WO2006/128965). The enzyme is reversible and specific for NADPH. In *Aspergillus niger* a D-galacturonic acid reductase, GAAA, was identified that could use NADPH and NADH, however NADPH had a higher affinity (Martens-Uzonova 2008). A gene ortholog of the *A. niger* gaaA exists also in *H. jecorina*, gar2, however it is not known whether it is functional (Martens-Uzonova 2008). The second enzyme in this pathway, a dehydratase, splits a water molecule from L-galactonic acid to generate 3-Deoxy-L-threo-hex-2-ulosonate (2-keto-3-deoxy-L-galactonic acid) (Kuorelahti et al. 2006). This enzyme reaction is not reversible. A deletion of the corresponding gene, lgd1, in the mould *H. jecorina* prevented the mould from growing on D-galacturonic acid, however when grown on a different carbon source, the deletion strain was converting D-galacturonate to L-galactonate (Kuorelahti et al. 2006). The third enzyme in the D-galacturonic acid pathway is the 3-Deoxy-L-threo-hex-2-ulosonate aldolase which is splitting the substrate 3-Deoxy-L-threo-hex-2-ulosonate into pyruvate and L-glyceraldehyde (Hilditch et al. 2007). The deletion of the aldolase gene, lgd1, in *Hypocrea jecorina* resulted in a strain unable to grow on D-galacturonic acid as a carbon source (Hilditch et al. 2007), however when grown on a different carbon source D-galacturonic acid was converted to 3-Deoxy-L-threo-hexylosonate (Hilditch et al. 2007). L-galactonic acid did not accumulate probably due to the activity of the L-galactonate dehydratase. Pyruvate can be metabolised trough different pathways whereas L-glyceraldehyde is not a metabolite of any known pathway.

L-Glyceraldehyde is converted to glycerol by the fourth enzyme of the pathway, an NADPH dependent reductase. A gene coding for an enzyme with this activity was identified in *H. jecorina* (Liepins et al. 2006). This enzyme, GLD1 in *H. jecorina*, was not reversible, i.e. the purified enzyme did not exhibit activity with glycerol and NADP. Martens-Uzonova analysed the transcriptome (the transcription of all genes) in the mould *A. niger*. In this work different carbon sources were compared including D-galacturonic acid, polygalacturonic acid and sugar beet pulp. It was noticed that the four genes of this catabolic pathway, here they are called gaaA, gaaB, gaaC and gaaD, were upregulated during growth on pectin and D-galacturonic acid (Martens-Uzonova 2008). Besides the genes required for catabolism and genes coding for pectinolytic enzymes also 3 genes coding for potential transport proteins were identified to be upregulated. It was suggested that these transporter proteins play a role in uptake of D-galacturonic acid (Martens-Uzonova 2008).

By "a nucleotide sequence encoding uronic acid dehydrogenase" is meant a gene encoding said enzyme, or a shortened or modified form of said gene being a functional equivalent of said gene.

The terms "nucleotide sequence", "nucleic acid sequence" and "DNA molecule" include both genome and cDNA.

A nucleotide sequence encoding uronate dehydrogenase enzyme EC 1.1.1.203 of the present invention can be isolated from any organism producing this enzyme comprising eukaryotes and including animals (and man), plants, fungi, yeasts or prokaryotes including bacteria. Preferably a nucleotide sequence encoding uronate dehydrogenase enzyme of the present invention is isolated from a microbial source, such as from bacteria or fungi, in particular from bacteria.

According to a preferred embodiment of the invention a nucleotide sequence encoding uronate dehydrogenase enzyme of the present invention is obtainable from genus *Agrobacterium*, more preferably from *A. tumefaciens*. According to a most preferred embodiment of the invention a nucleotide sequence encoding the enzyme is obtainable from a commercial culture collection strain C 58, ATCC, American Type Culture Collection. According to another preferred embodiment of the invention a nucleotide sequence encoding uronate dehydrogenase enzyme is obtainable from genus *Pseudomonas*. According to a most preferred embodiment of the invention a nucleotide sequence encoding the enzyme is available as GenBank accession number EU377538.

The origin of a nucleotide sequence encoding uronate dehydrogenase enzyme of the present invention is not restricted to the genus *Agrobacterium* or to the species *A. tumefaciens* or is not restricted to genus or species of *Pseudomonas*. By using the description provided herein, a person skilled in the art can find and isolate a nucleotide sequence encoding uronate dehydrogenase enzyme of the present invention from other genera of bacteria or fungi or from other organisms.

Organisms capable of producing uronate dehydrogenase enzyme can be screened, the activity on various substrates can be determined, and the enzyme characterized. Nucleotide sequences encoding uronate dehydrogenase enzyme in various organisms can be isolated and the amino acid sequences encoded by the nucleotide sequences can be compared with the amino acid sequence of the uronate dehydrogenase enzyme isolated and characterized in the Examples here. A person skilled in the art can also identify a conserved region in the nucleotide or amino acid sequence and clone a gene fragment using PCR techniques. After sequencing the fragment the complete gene can be obtained for example by using cDNA library in a vector as described by Richard et al. (2001). A nucleotide sequence encoding uronate dehydrogenase enzyme can be identified also by nucleic acid hybridization.

Standard molecular biology methods can be used in the cloning of the uronate dehydrogenase enzyme i.e. in the isolation and enzyme treatments of DNA, in *E. coli* transformations, the isolation of a fragment comprising the uronate dehydrogenase gene by amplification in a PCR reaction (Coen D M, 2001) and in the techniques for codon change. The basic methods used are described in the standard molecular biology handbooks, e.g. Sambrook et al. (1989) and Sambrook and Russell (2001). Insertion of the nucleotide sequence under a strong promoter in an expression vector, transfer of the vector into suitable host cells and cultivation of the host cells in conditions provoking production of said enzyme. Methods for protein production by recombinant technology in different host systems are well known in the art (Gellissen, 2005).

By "a homologous nucleotide sequence" is meant a nucleotide sequence originating from the same species as the host. By "a heterologous nucleotide sequence" is meant a nucleotide sequence from another species as the host or from other genera as the host. If the host organism is prokaryotic host, for example a bacterial host, such as *E. coli*, *Agrobacterium* or *Pseudomonas*, the nucleotide sequence encoding uronate dehydrogenase may be homologous. If the host organism is a eukaryotic organism, for example a fungus, the heterologous nucleotide sequence may mean a nucleotide sequence from a prokaryote, such as from bacteria.

It is evident that small variations in the nucleotide sequence of a gene do not significantly change the catalytic properties of the encoded protein. For example many changes in the nucleotide sequence do not change the amino acid sequence of the encoded protein. Also an amino acid sequence may have variations, which do not change the functional properties of a protein, in particular they do not prevent an enzyme from carrying out its catalytic function. Such variations in the nucleotide sequence or DNA molecules or in an amino acid sequence are known as "functional equivalents", because they do not significantly change the function of the gene to encode a protein with a particular function, e.g. catalyzing a particular reaction or, respectively, change the particular function of the protein. Thus such functional equivalents, including fragments, of the nucleotide sequence SEQ ID NO:3 or 19, and of the amino acid sequence SEQ ID NO:4 or 20, respectively, are encompassed within the scope of invention.

Within the scope of the present invention are also nucleotide sequences that are capable of hybridizing with the identified sequences under intermediate or high stringency conditions. For example, intermediate stringency hybridization conditions can be performed in a hybridization mixture containing 6×SSC (0.9 M NaCl in 0.09 M sodium citrate, pH 7), 0.5% sodium dodecyl sulfate (SDS), 5×Denhardt's solution and 100µ/ml of Herring Sperm DNA at 50° C. High stringency hybridization can be performed for example in the same hybridization mix at 68° C.

By the term "identity" is here meant the identity between two amino acid sequences compared to each other from the first amino acid encoded by the corresponding gene to the last amino acid. The identity of the full-length sequences is measured by using Needleman-Wunsch global alignment program at EMBOSS (European Molecular Biology Open Software Suite; Rice et al., 2000) program package, version 2.9.0, with the following parameters: EMBLOSUM62, Gap penalty 10.0, Extend penalty 0.5.

Within the scope of the present invention are enzymes or polypeptides which comprise amino acid sequences which have uronate dehydrogenase activity and which show at least 65% identity to the amino acid sequence SEQ ID NO:4 or SEQ ID NO:20. Preferred enzymes comprise amino acid sequences which show at least 70%, more preferably at least 75%, even more preferably at least 80 identity. Still more preferable the amino acid sequences show at least 85%, more preferably at least 90%, still more preferably at least 95%, most preferably at least 98% identity to the amino acid sequence SEQ ID NO:4 or SEQ ID NO:20.

According to one preferred embodiment of the present invention a nucleotide sequence encoding uronate dehydrogenase is identified and expressed in a host microorganism. The host may be prokaryotic or eukaryotic host. Preferably the host is eukaryotic, more preferably a fungal host, most preferably a filamentous fungal host. The nucleotide sequence encoding uronate dehydrogenase encodes preferably uronate dehydrogenase of the oxidative pathway for uronic acid catabolism of bacteria.

The invention is not restricted to genetically modifying moulds or yeasts. The nucleic acid sequence encoding the uronate dehydrogenase enzyme can be expressed in any organism, such as bacteria, plants or higher eukaryotes by applying the genetic tools suitable and known in the art for that particular organism. The microorganism should therefore be interpreted broadly to include also cell of higher organisms.

The present invention was exemplified by identifying and expressing a nucleotide sequence encoding uronic acid dehydrogenase in a fungal microorganism. The recombinant organism was shown to be able to convert D-galacturonic acid to mucic acid (meso-galactaric acid) and D-glucuronic acid to sacchraric acid (D-glucaric acid). The nucleotide sequence encoding uronic acid dehydrogenase was from bacterial origin.

The expression of uronate dehydrogenase in a fungal host is of advantage, since many fungal hosts, in particular moulds, produce pectinolytic enzymes. Suitable fungal hosts are host strains from for example *Fusarium*, *Aspergillus* and *Hypocrea* (earlier *Trichoderma*) genera, preferably *Aspergillus* and *Hypocrea*. More specifically suitable host strains belong to *H. jecorina* or *A. niger* species. The production of pectinolytic enzymes would facilitate the making of D-galacturonic acid from pectin.

Suitable expression and production host systems are for example the production system developed for the fungus host *Trichoderma* (EP 244 234) (species of *Hypocrea* were earlier classified to *Trichoderma*), or *Aspergillus* production system, such as *A. oryzae* or *A. niger* (WO 9708325 and WO 9533836, U.S. Pat. No. 5,843,745, U.S. Pat. No. 5,770,418), or the production system developed for *Fusarium*, such as *F. oxysporum* (Malardier et al., 1989).

The cloning of genes coding for the uronate dehydrogenase in two different species of filamentous fungi and a yeast was exemplified in the examples. The same approach can be used with other filamentous fungi, yeast or any microorganism.

The host organism of the present invention might be naturally utilizing hexuronic acids. To prevent the natural pathway from competing for hexuronic acid the competing pathways can be knocked out. The nucleotide sequence encoding the enzyme can be inactivated for example by preventing its expression or by mutation or deletion of the coding sequence. These techniques typically makes use of the nucleotide sequence of the coding sequence or of the nucleotide sequence adjacent to the coding sequence. The coding sequence of the enzyme can be inactivated in any microorganism having said nucleotide sequence.

The knocking out of a natural pathway for utilisation of D-galacturonic acid can be done for example by deleting the D-galacturonic acid reductase.

It is therefore still another embodiment of this invention that in addition to the heterologous expression of uronate dehydrogenase the endogenous pathway for hexuronate catabolism is interrupted. The interruption of this catabolic pathway has been exemplified by deleting D-galacturonic acid reductase, more specifically gar1 in *H. jecorina* and the gaaA gene in *Aspergillus niger*. These two genes have a low sequence homology and different kinetic properties. The gaaA has a close homologue called gar2 in *H. jecorina* (Martens-Uzonova 2008). Because of the redundancy of homologue sequences it was unexpected that the single deletion of gar1 or gaaA was sufficient to bring the catabolism to a halt. Another unexpected result was that the gar1 and gaaA deletion mutants survive in the presence of D-galacturonic acid. It could have been expected that such a deletion causes D-galacturonic acid to be toxic similar to a pgi1 deletion in *S. cerevisiae*. In the yeast *S. cerevisiae* the pgi1 gene codes for the phosphofructo isomerase, the deletion of which results in glucose toxicity. The immediate reaction product of uronic acid dehydrogenase is probably the galactarate lactone (Wagner and Hollmann 1976). The lactone is hydrolysing to galactarate spontaneously; however it might be advantageous to coexpress a lactonase that would facilitate the hydrolysis of the lactone.

If the uronate dehydrogenase is expressed in a host, which is not naturally utilising hexuronic acids, there is no need to knock out competing pathways. However, here the transport of hexuronic acid into the cell might slow down the conversion of hexuronic acids to hexaric acids. If for example the D-galacturonic acid dehydrogenase is expressed in a host, which is not naturally utilising D-galacturonic acid, there is no need to knock out competing pathways. Here the transport of D-galacturonic acid into the cell might slow down the conversion of D-galacturonic acid to mucic acid. In this case the expression of genes coding for D-galacturonic acid transport molecules can facilitate the conversion of uronic acids.

For example, if the host is yeast, such as *S. cerevisiae*, the introduction of a transporter to facilitate the transport of D-galacturonic acid, D-glucuronic acid and 7 or D-mannuronic acid or into the cell is recommended.

The enzyme activity of the uronate dehydrogenase has been described previously by Chang and Feingold (1969) and references therein. Chang and Feingold (1969) described a partly purified NAD-dependent dehydrogenase, which had activity with D-galacturonic and D-glucuronic acid.

In the present description there has been described a different procedure for the purification of the enzyme. In this description has been used the technique of tryptic digestion of the purified protein and subsequent MALDI-ToF analysis to identify the sizes of the protein fragments. Since the genome sequence of this organism was known, the knowledge of the protein fragments enabled us to identify the corresponding gene. It is believed that a gene sequence coding for a uronate dehydrogenase has been described here the first time. There is an entry in the NCBI sequence database (National Center for Biotechnology Information, USA, www.ncbi.nlm.nih.gov) with the GenBank accession number EU377538 which describes an uronate dehydrogenase from *Pseudomonas syringae* pv. tomato str. DC3000 with the EC number EC 1.1.1.203. This database entry did not contain any further details to substantiate that the gene was indeed a uronate dehydrogenase.

Within the scope of the present invention are also genetic constructions comprising a suitable vector which can be used when the nucleic acid sequence encoding the uronate dehydrogenase enzyme is introduced into a host. In the construction the nucleotide sequence is typically operable linked to regulatory regions facilitating the expression of the nucleotide sequence, such as a promoter and signal sequence. The vector can be for example a virus, such as a bacteriophage or a plasmid.

In the examples strong and constitutive promoters were used for the expression of the uronate dehydrogenase. Other more or less strong promoters or regulated promoters can be used.

Suitable biomaterial for the invention is biomass comprising sugar, sugar acids or derivatives thereof, in particular comprising hexuronic acids. Suitable biomaterial is for example sugar beet pulp, which comprises pectin. Also other pectin comprising materials may be used. Other suitable biomaterials are effluents and side streams of pulp and paper industry or biomaterial comprising algae.

According to an embodiment of the invention, in the method of converting hexuronic acid to hexaric acid, a microbial host strain genetically modified to express uronate dehydrogenase enzyme (EC 1.1.1.203) is contacted with a biomaterial comprising hexuronic acid in order to convert at least a portion of the hexuronic acid to hexaric acid. The conversion products are recovered.

Thus, according to this embodiment, biomass comprising a sugar acid or a derivative thereof is fermented by a microorganism capable of converting hexuronic acid to hexaric acid and the desired compounds produced are recovered.

In another embodiment, the present invention is directed to a method, which comprises cultivating a genetically modified microorganism under conditions allowing expression of the protein in the presence of hexuronic acids.

The present invention also comprises methods for recovery of the enzyme protein or recovery of the conversion products.

The invention is not only restricted to the oxidation of D-galacturonic acid to mucic acid. D-glucuronic acid as well as D-mannuronic acid, which is the principal component of alginate, can be oxidised to D-glucaric and D-mannaric acid respectively.

The uronate dehydrogenase enzyme can be used by growing the host organism on a substrate comprising hexuronic acids, such as D-galacturonic acid, D-glucuronic acid or D-mannuronic acid. The culture conditions can be made suitable for the growth and proliferation of the host organism.

The invention is further directed to an enzyme preparation comprising the uronate dehydrogenase enzyme. Such a preparation may be a crude cell extract of the genetically modified organism, a spent culture medium or the enzyme may be further purified from the cell extract or from the culture medium, whereby the preparation comprises at least the enzyme in purified form. The preparation may also comprise other enzymes taking part in the catabolism of sugars, or sugar acids or their derivatives.

The uronate dehydrogenase enzyme can be used as an enzyme preparation. The term "enzyme preparation" denotes here to any enzyme product, which contains at least uronate dehydrogenase enzyme. Thus, such an enzyme preparation may be a spent culture medium or filtrate containing one or more uronate dehydrogenase optionally with other enzymes, an isolated uronate dehydrogenase enzyme or a mixture of one or more uronate dehydrogenase enzymes. In addition to the uronate dehydrogenase activity, such a preparation may contain additives, such as mediators, stabilizers, buffers, preservatives, surfactants and/or culture medium components. Preferred additives are such, which are commonly used in enzyme preparations intended for the application, where the enzyme preparation is used. The enzyme preparation may be in the form of liquid, powder or granulate.

The enzyme preparation may comprise in addition to uronate dehydrogenase, one or more other enzymes, which may be for example pectinolytic enzymes, amylases and/or cellulases. Alternatively, before, during or after the uronate dehydrogenase treatment of the present invention, another enzyme treatment may be carried out.

The invention is illustrated by the following non-limiting examples. It should be understood, however, that the embodiments given in the description above and in the example are for illustrative purposes only, and that various changes and modifications are possible within the scope of the claims.

EXAMPLE 1

Cloning and Expression of the D-galacturonic Acid Dehydrogenase in a Heterologous Host A commercial culture collection strain CS58 of *Agrobacterium tumefaciens* (*Rhizobium radiobacter*) was grown in a minimal medium containing D-galacturonic acid. The cells were lysed by sonication and the protein extract was then bound to a DEAE column and eluted with a linear salt gradient. The fractions were tested for D-galacturonic acid dehydrogenase activity using D-galacturonic acid and NAD reaction as the substrates by measuring the NADH production by following the absorption at 340 nm. The active fractions were concentrated and applied to a non-denaturating PAGE. After separation the active fraction was identified using zymogram staining.

The active fractions were identified and separated on an SDS-PAGE. A 32 kDa protein band was identified as the D-galacturonic acid dehydrogenase. The protein band was cut from the gel, digested with trypsin and the resulting peptides were analyzed using MALDI TOF. The following peptide masses were obtained: 665.4160, 966.4224, 1020.4779, 1029.5153, 1407.4625, 1720.6669, 1740.7902 and 2082.9321. These peptide masses were then used to identify the corresponding gene in the *A. tumefaciens* genome. The open reading frame was then amplified by PCR introducing EcoRI and BamHI restrictions sites. The following primers were used 5'-CACAGCAAAGACGCAGAATTCGCTTG-GAAG-3' (SEQ ID NO:1) and 5'-GGCTTGGGATCCCGCT-GATCATTCAGCTC-3' (SEQ ID NO: 2). The gene was called uro1 and the sequence of the open reading frame is SEQ ID NO:3 in the sequence listing. The sequence SEQ ID NO:3 encodes the amino acid sequence SEQ ID NO:4.

The PCR product was then ligated to a TOPO vector (Invitrogen). The EcoRI-BamHI fragment was released from the TOPO vector and ligated to a yeast expression vector. The expression vector was a multicopy expression vector for *S. cerevisiae* containing the URA3 for selection and the constitutive TPI promoter. The plasmid was derived from the pYX212 plasmid (R&D Systems); it was modified to have a BamHI restriction site in the multiple cloning site. The derived vector was transfected to the *Saccharomyces cerevisiae* strain CEN.PK.

EXAMPLE 2

Characterization of the Enzyme Activity

The *S. cerevisiae* strain resulting from the Example 1 was then disintegrated by vortexing with glass beads and the yeast extract analysed for D-galacturonic acid dehydrogenase activity. In a control experiment a similar strain but with an empty plasmid was used. To assay the D-galacturonic acid dehydrogenase activity the crude cell extract was mixed with 0.5 mM NAD and 4 mM D-galacturonic acid in a 50 mM Tris pH 7.5 buffer containing 0.5 mM $MgCl_2$. The activity was 0.12 units per mg of extracted protein. One unit is the activity that forms 1 µmol of product per minute. In the control strain no activity could be detected.

EXAMPLE 3

Characterization of the Purified Histidine-Tagged D-galacturonic Acid Dehydrogenase The D-galacturonic acid dehydrogenase with a histidine-tag at the N-terminal end was produced in a similar manner as in the Example 1, except that the histidine-tag was introduced by PCR. To introduce the histidine tag the following primers were used 5'-CCGGAATTCACCATGCACCACCATCAC-CATCACATGGCGATGAAACGGCTTCTTG-3' (SEQ ID NO:5) in sense direction and 5'-GGCTTGGGATCCCGCT-GATCATTCAGCTC-3' (SEQ ID NO:6) in anti-sense. After the expression of the histidine-tagged protein in *S. cerevisiae* as described in the Example 1 the activity was measured as described in the Example 2. The histidine tagged protein exhibited the same activity as the non-tagged protein in the yeast extract. The histidine-tagged D-galacturonic acid dehydrogenase was then purified using a Ni-NTA-agarose (Qiagen) according to the instructions of the manufacturer. The purified enzyme gave a single band in an SDS PAGE.

The protein was active with D-galacturonic acid and D-glururonic acid (GlcUA).

The purified protein was then used to estimate the Michaelis-Menten constants. For D-galacturonic acid a Km of 0.5 mM and a Vmax of 124 units per mg of protein (Km (GlcUA) =1.1 mM Vmax (GlcUA 221 units per mg of protein) and for NAD a Km of 0.9 mM and a Vmax of 145 units per mg of protein were estimated.

EXAMPLE 4

Deletion of the D-galacturonic Acid Reductase in *H. jecorina*

For the deletion of the gar1 gene a deletion cassette was constructed. To obtain the deletion cassette 1.5 kb areas of genomic DNA from both sides of the D-galacturonic acid reductase gene were cloned by PCR from *H. jecorina* genomic DNA. The following primers were used:

```
gar1 5f:
                                         (SEQ ID NO: 7)
GTAACGCCAGGGTTTTCCCAGTCACGACGAAGCTTATATCCACCGT-
GTCCCAG gar1 5r:
                                         (SEQ ID NO: 8)
ATCCACTTAACGTTACTGAAATCTCCAACGACGCAGTTGTTTGAG-
CAAC gar1 3f:
                                         (SEQ ID NO: 9)
CTCCTTCAATATCATCTTCTGTCTCCGACTTGCATTGGTCAGAGCG-
GTA gar1 3r:
                                         (SEQ ID NO: 10)
GCGGATAACAATTTCACACAGGAAACAGCAAGCTTAAGCAGTGGAT-
GACTTGCTG
```

The other elements for the construction of the deletion cassette were the hph (hygromycin B phosphotransferase) gene under *Aspergillus* trpC promoter and the elements for replication and selection in yeast and *E. coli*. The hph containing fragment was obtained by PCR using the pCSN44 as a template and using the following primers:

```
hphF
GTCGGAGACAGAAGATGATATTGAAGGAGC    (SEQ ID NO: 11)

hphR
GTTGGAGATTTCAGTAACGTTAAGTGGAT     (SEQ ID NO: 12)
``` to produce a PCR fragment of 1.447 bp.

The fragment for replication and selection in *S. cerevisiae* and *E. coli* was obtained by digesting the pRS426 with the restriction enzymes EcoRI and XhoI to release a 5.7 kb fragment. The two fragments obtained by PCR that contained the flanking regions for homologous recombination were combined with the other fragments. All four DNA fragments were then transformed to the *S. cerevisiae* strain FY834. The single plasmid obtained through homologues recombination was isolated from the *S. cerevisiae* strain and amplified in *E. coli*. pCSN44, pRS426 and FY834 were obtained from Jay C. Dunlap. The deletion cassette, 4520 bp containing the gar1 flanking regions and the hygromycin B resistance, was then released by HindIII digestion and transformed to the *H. jecorina* strain QM6a. Transformants were selected for the resistance to hygromycin. Strains with a successful deletion were identified by colony PCR. To test if the mutant strains were still able to catabolise D-galacturonic acid a growth experiment was performed. The QM6a and mutant strain were grown on a medium in the presence and absence of 1% D-galacturonic acid as described previously (Kuorelahti et al. 2006) After inoculating $10^7$ spores per 50 ml the QM6a produced a dry mass of about 3 g/l in the presence and about 0.24 g/l in the absence of D-galacturonic acid after 5 days of incubation. The mutant strains produced 0.4-0.6 g/l in the presence of D-galacturonic acid and about 0.24 g/l in the absence of D-galacturonic acid under similar conditions.

EXAMPLE 5

Expression of the *A. tumefaciens* D-galacturonic Acid Dehydrogenase in the *H. jecorina* D-galacturonic Acid Reductase Deletion Strain A gar1 deletion strain from example 4 was used to express the *A. tumefaciens* D-galacturonic acid dehydrogenase uro1 from example 1. The BamHI fragment containing the uro1 was released from the TOPO vector described in the Example 1 and the uro1 gene was ligated to the BamHI site of the modified pAN53-1 NotI vector described by Kuorelahti et al., 2006. It was checked that the orientation of the uro1 was suitable for transcription. The resulting plasmid was then cotransformed into the gar1 deletion strain with a selection plasmid pTOC202 that has the *A. nidulans* amdS gene coding for acetamidase as a marker. Transformants were selected for growth in the presence of acetamide. The transformants were also verified by PCR and by testing the crude extract of the mycelia for D-galacturonic acid dehydrogenase activity. The activity in the transformants were 1.3-1.5 nkat per mg of extracted protein. In the control strain no activity was detected. The transformants were also used for a fermentation experiment to convert D-galacturonic acid to mucic acid. For that purpose mutant and control strains were tested as described in Example 4 except that the medium contained 1% D-xylose in addition to the 1% D-galacturonic acid. The D-xylose was added to allow the strains to grow since the mutant strain is unable to grow on D-galacturonic acid. After 3 days the mutant strains expressing the uro1 had produced between 1 and 1.3 g/l of mucic acid while the control strain, which only contained the gar1 deletion, did not produce detectable amounts of mucic acid.

EXAMPLE 6

Deletion of the *Aspergillus niger* D-galacturonic Acid Dehydrogenase

For the deletion of the GaaA gene in *Aspergillus niger* a deletion cassette was constructed. To obtain the deletion cassette 1.5 kb areas of genomic DNA from both sides of the D-galacturonic acid dehydrogenase gene were cloned by PCR from *A. niger* genomic DNA. The following primers were used:

```
gaaA-5-F:
TATACTCGAGTGAATTGCACTCTTCGTACCG    (SEQ ID NO: 13)

gaaA-5-R:
TATACCATGGTGTGATTGCTGTGGTGTAAAT    (SEQ ID NO: 14)

gaaA-3-F:
TATACCATGGCCGTTTATGATTCTGGTCCATC   (SEQ ID NO: 15)

gaaA-3-R:
TATAGAATTCTCGAGTTAATTCCCTTAGCG     (SEQ ID NO: 16)
```

The other element for the construction of the deletion cassette was the pyrG (orotidine-5'-phosphate decarboxylase) gene from *Aspergillus niger*. The pyrG fragment containing its own promoter and terminator was obtained by PCR from *A. niger* genomic DNA. The following primers were used:

```
pyrG-del-F_n:
TATACCCGGGTGATTGAGGTGATTGGCGAT     (SEQ ID NO: 17)

pyrG-del-R_n:
TATACCCGGGTTATCACGCGACGGACAT       (SEQ ID NO: 18)
```

The GaaA-deletion fragments (gaaA flanking regions) were first inserted into pRSET-A vector (XhoI-EcoRI sites) by conventional restriction-ligation cloning approach. The pyrG DNA fragment was inserted into NcoI site (Klenow polymerase and Antarctic phosphatase treated) created between the two gaaA deletion fragments. Resulting construct (FIG. 3) was confirmed by restriction digestion and sequencing. The deletion cassette, 4854 bp containing the gaaA flanking regions and the pyrG gene, was then released by NheI digestion and transformed to an *A. niger* strain where the pyrG gene was deleted.

Transformants were selected for the growth in the absence of uracil. Strains with a successful deletion were identified by PCR. To test if the mutant strains were still able to catabolise D-galacturonic acid a growth experiment was performed. The ATCC1015-pyrG (parental strain) and mutant strains (two clones obtained) were grown on a medium in the presence of 2% D-galacturonic acid as a sole carbon source. The mutant strains were not able to grow under these conditions (FIG. 4).

EXAMPLE 7

Figure 6:
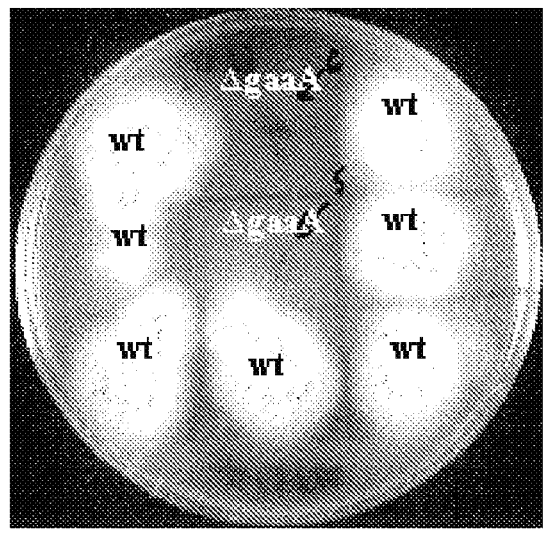
FIG. 6. The ATCC1015-pyrG (parental strain) and mutant strains (two clones obtained) were grown on a medium in the presence of 2% D-galacturonic acid as a sole carbon source. The mutant strains were not able to grow under these conditions.
Figure 7:
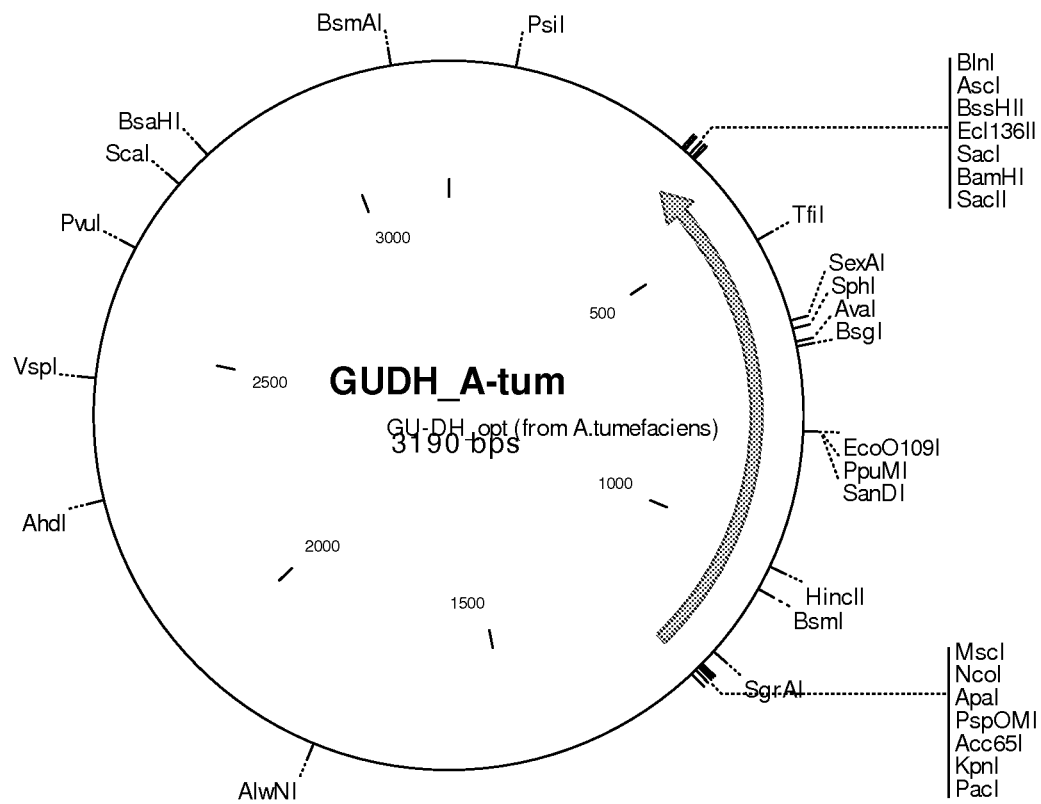
FIG. 7 shows plasmid GUDH_A-tum.

Expression of the *A. tumefaciens* D-galacturonic Acid Dehydrogenase in the *A. niger* D-galacturonic Acid Reductase Deletion Strain The gaaA deletion strain from example 6 was used to express the *A. tumefaciens* D-galacturonic acid dehydrogenase uro1. The uro1 gene was codon optimized for the expression in *A. niger*. ApaI-Ecl136II fragment from the p-GU-DH plasmid (FIG. 6) containing the uro1 gene was ligated to the ApaI-SpeI (Klenow filled-in) sites of the modified pCL2 vector containing *A. nidulans* amdS gene as a selection marker. The resulting plasmid (FIG. 7) was then transformed into the gaaA deletion strain. Transformants were selected for the growth in presence of acetamide as a sole nitrogen source. The transformants were also verified by PCR and by testing the crude extract of the mycelia for D-galacturonic acid dehydrogenase activity. The crude extract of the transformants showed D-galacturonic acid dehydrogenase activity while in the control strain no activity was detected. The transformants were also used for a fermentation experiment to convert D-galacturonic acid to mucic acid. For that purpose mutant and control strains were tested as described in Example 5. After 3 days the mutant strains expressing the uro1 had produced mucic acid while the control strain, which only contained the gaaA deletion, did not produce detectable amounts of mucic acid.

EXAMPLE 8

Expression of Uronate Dehydrogenase from *Pseudomonas*

The DNA coding for uronate dehydrogenase was customsynthesised by GENEART. The codes for the same amino acid as the gene with the GenBank accession number EU377538. The DNA sequence is in the Sequence Listing SEQ ID NO: 19. It codes for the amino acid sequence SEQ ID NO:20.

The open reading frame was released by digestion with NcoI and SpeI. The resulting fragment was then ligated to the NcoI and NheI sites of the pYX212 (R&D Systems) which is a multicopy yeast expression vector with PGK1 promoter and URA3 selection marker. The resulting vector was then transfected to the *S. cerevisiae* strain CEN.PK as in the Example 1. The enzyme activity was then tested as in Example 2. The uronate dehydrogenase showed activity with NAD and D-galacturonic acid and with NAD and D-glucuronic acid.

EXAMPLE 9

Expression of a Transporter Gene for D-galacturonic Acid in *S. Cerevisiae* in Combination with the Expression of Uronate Dehydrogenase For the expression of a D-galacturonic acid transporter in *S. cerevisiae* a gene coding for a D-galacturonic acid transporter from *Aspergillus niger* (Martens-Uzonova, 2008) was synthesised and a vector for the expression in *S. cerevisiae* was constructed. The resulting plasmid was transformed to the yeast strain already containing the uronate dehydrogenase from *Agrobacterium tumefaciens* or from *Pseudomonas*. Fermentation in the presence of D-galacturonic acid resulted in the production of mucic acid.

EXAMPLE 10

Figure 8:
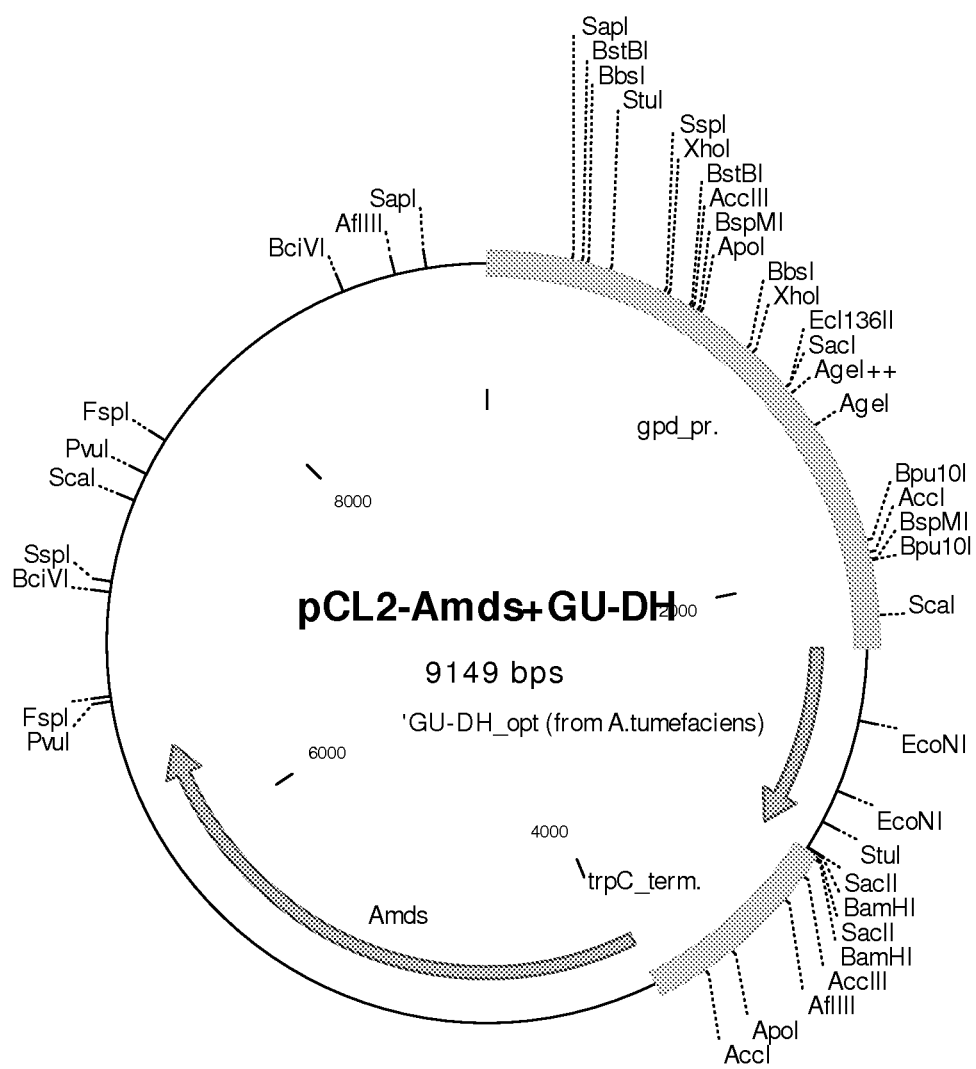
FIG. 8 shows plasmid pCL2-Amf'ds+GU-DH
Figure 11:
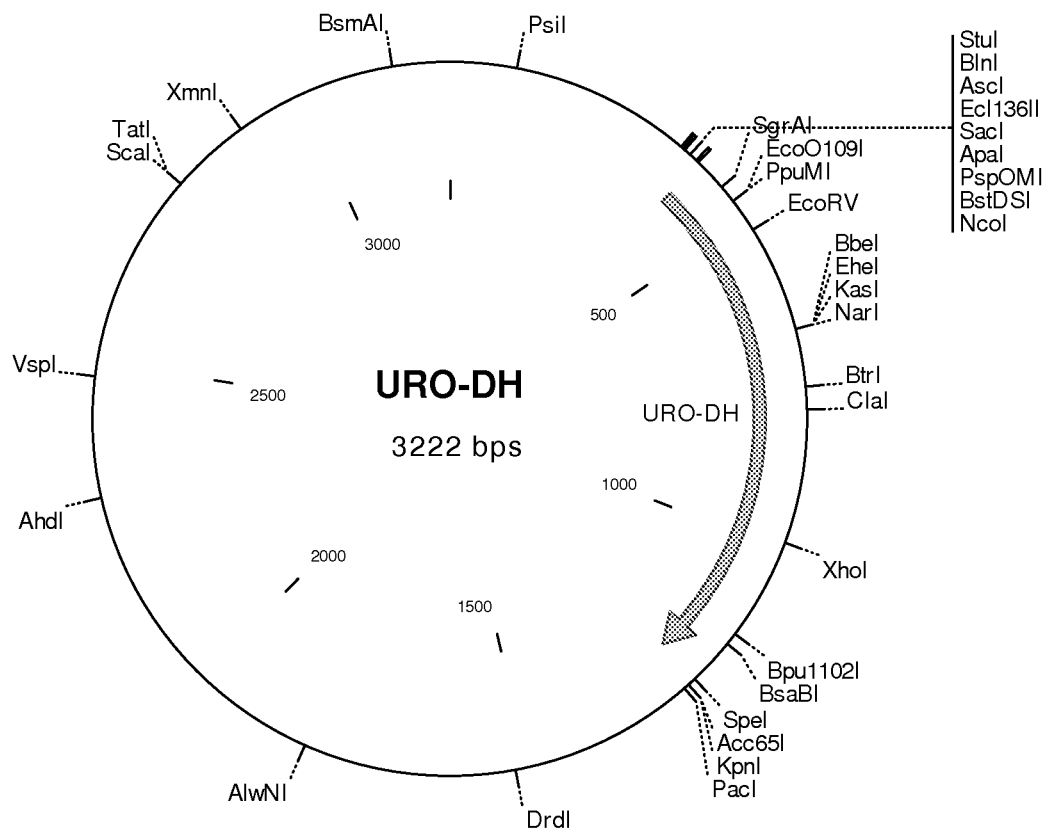
FIG. 11 shows plasmid URO-DH.
Figure 12:
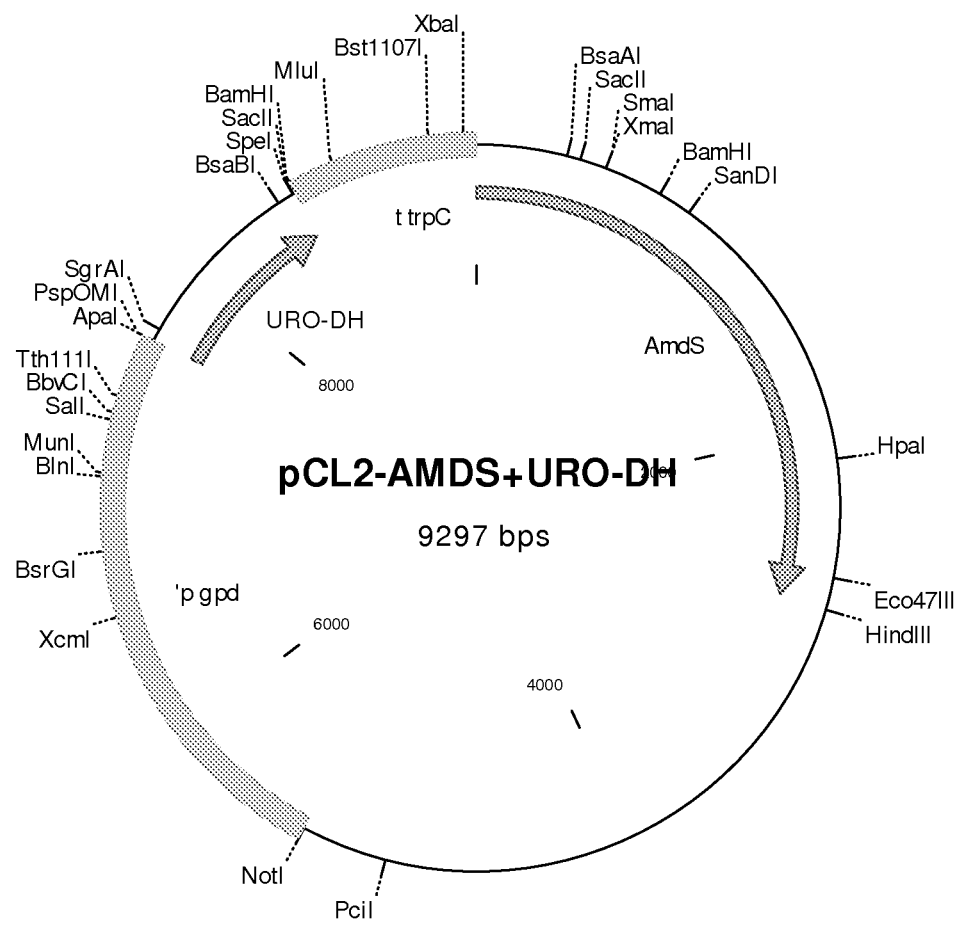
FIG. 12 shows plasmid pCL2-AMDS+URO-DH

Expression of Uronate Dehydrogenase from *Pseudomonas* in the *A. niger* D-galacturonic Acid Reductase Deletion Strain The gaaA deletion strain from example 6 was used to express the uronate dehydrogenase from *Pseudomonas* (from example 8). The gene was codon optimized for the expression in *A. niger*. ApaI-SpeI fragment from the p-URO-DH plasmid (FIG. 7) containing the uronate dehydrogenase gene was ligated to the ApaI-SpeI sites of the modified pCL2 vector containing *A. nidulans* amdS gene as a selection marker. The resulting plasmid (FIG. 8) was then transformed into the gaaA deletion strain. Transformants were selected for the growth in the presence of acetamide as a sole nitrogen source. The transformants were also verified by PCR and by testing the crude extract of the mycelia for D-galacturonic acid dehydrogenase activity. The crude extract of the transformants showed D-galacturonic acid dehydrogenase activity while in the control strain no activity was detected. The transformants were also used for a fermentation experiment to convert D-galacturonic acid to mucic acid. For that purpose mutant and control strains were tested as described in Example 5. After 3 days the mutant strains expressing the uronate dehydrogenase had produced mucic acid while the control strain, which only contained the gaaA deletion, did not produce detectable amounts of mucic acid.

REFERENCES

Chang Y F, Feingold D S (1969) Hexuronic acid dehydrogenase of *Agrobacterium tumefaciens*. J. Bacteriol. 99:667-673

Chang Y F, Feingold D S (1970) D-glucaric acid and galactaric acid catabolism by *Agrobacterium tumefaciens*. J. Bacteriol. 102:85-96

Coen D. M. 2001 The polymerase chain reaction, published in Ausubel F M, Brent R, Kingston R E, More D D, Seidman J G, Smith K. and Struhl K (eds.) Current protocols in molecular biology. John Wiley & Sons. Inc., Hoboken, USA)

Gellissen G, (ed). 2005. Production of recombinant proteins. Novel microbial and eukaryotic expression systems. Wiley-VCH Verlag GmbH & Co. Weinheim, Germany.

Hilditch S, Berghall S, Kalkkinen N, Penttila M, Richard P (2007) The missing link in the fungal D-galacturonate pathway: identification of the L-threo-3-deoxy-hexylosonate aldolase. J Biol. Chem. 282:26195-26201

Jeffcoat R (1975) Studies on the subunit structure of 4-deoxy-5-oxoglucarate hydrolyase (decarboxylating) from *Pseudomonas acidovorans*. Biochem J. 145:305-309

Kuorelahti S, Jouhten P, Maaheimo H., Penttilä M, Richard P (2006) L-galactonate dehydratase is part of the fungal path for D-galacturonic acid catabolism. Mol. Microbiol. 61:1060-1068

Kuorelahti S, Kalkkinen N, Penttilä M, Londesborough J, Richard P (2005) Identification in the mold *Hypocrea jecorina* of the first fungal D-galacturonic acid reductase. Biochemistry 44:11234-11240

Liepins J, Kuorelahti S, Penttilä M, Richard P (2006) Enzymes for the NADPH-dependent reduction of dihydroxyacetone and D-glyceraldehyde and L-glyceraldehyde in the mould *Hypocrea jecorina*. Febs J. 273:4229-4235.

Malardier L, M J Daboussi, J Julien, F Roussel, C Scazzocchio and Y Brygoo. 1989. Gene 15:147-156.

Martens-Uzonova E (2008) Assessment of the pectinolytic network of *Aspergillus niger* by functional genomics. Insight from the transcriptome. In. PhD thesis, University of Wageningen, Wageningen Richard et al. (2001) J. Biol. Chem. 276: 40631-40637.

Wagner G, Hollmann S (1976) Uronic acid dehydrogenase from *Pseudomonas syringae*. Purification and properties. Eur J. Biochem. 61:589-596

---

What is claimed is:

1. A method for converting galacturonic acid to galactaric acid, said method comprising contacting a eukaryotic microbial host strain genetically modified to express uronate dehydrogenase enzyme (EC 1.1.1.203) comprising an amino acid sequence according to SEQ ID NO:4 with a biomaterial comprising galacturonic acid and recovering conversion products comprising galactaric acid.

2. The method according to claim 1, wherein the host is a fungal host, preferably a fungal host being naturally capable of degrading pectin.

3. The method according to claim 2, wherein the host belongs to *Aspergillus* or *Hypocrea* genera.

4. The method according to claim 3, wherein D-galacturonic acid is converted to mucic acid.

5. The method according to claim 1, wherein the endogenous pathway for hexuronate catabolism has been interrupted in the host.

6. The method according to claim 5, wherein the endogenous pathway of D-galacturonic acid reductase has been deleted.

7. The method according to claim 2, wherein the host is a yeast host belonging to *Saccharomyces* genus.

8. The method according to claim 1, wherein the nucleotide sequence encoding uronate dehydrogenase enzyme (EC 1.1.1.203) originates from *Agrobacterium* genera.

9. The method according to claim 1, wherein the host expresses hexuronic acid transport molecules.

10. A method for treating biomaterial comprising galacturonic acid, said method comprising a step of a eucaryotic microbial host strain genetically modified to express uronate dehydrogenase enzyme (EC 1.1.1.203) comprising an amino acid sequence according to SEQ ID NO:4 being contacted with said biomaterial under suitable culture conditions.

11. A genetically modified eukaryotic microbial host strain expressing uronate dehydrogenase enzyme (EC 1.1.1.203) comprising amino acid sequence according to SEQ ID NO:4 and converting galacturonic acid to galactaric acid.

12. The host strain according to claim 11, wherein the host is a fungal host.

13. The host strain according to claim 12, wherein the host strain belongs to *Aspergillus* or *Hypocrea* genera.

14. The host strain according to claim 11, wherein the host strain is capable of converting D-galacturonic acid to mucic acid.

15. The host strain according claim 11, wherein endogenous pathway for hexuronate catabolism has been interrupted in the host strain.

16. The host strain according to claim 15, wherein D-galacturonic acid reductase encoding gene in the host strain has been deleted.

17. The host strain according to claim 12, wherein the host strain is a yeast host.

18. The host strain according to claim 11, wherein the host strain has been genetically modified to express a nucleotide sequence selected from the group consisting of:
    (a) a nucleotide sequence encoding a polypeptide comprising amino acid sequence SEQ ID NO: 4 and having uronate dehydrogenase enzyme (EC 1.1.1.203) activity;
    (b) a nucleotide sequence comprising the coding sequence of nucleotide sequence SEQ ID NO:3; and
    (c) a nucleotide sequence which hybridizes under stringent conditions to the nucleotide sequences in step (a), or (b) wherein hybridization is performed in a hybridization mixture containing 6×SSC, pH 7 at a temperature of 50° C.

19. The host strain of claim 12, wherein the fungal host is naturally capable of degrading pectin.

20. The host strain of claim 17, wherein the host belong to genus *Saccharomyces*.

21. A genetically modified fungal host strain transformed with a bacterial nucleotide sequence encoding a protein having uronate dehydrogenase enzyme activity (EC 1.1.1.203) comprising amino acid sequence according to SEQ ID NO:4 and said host strain converting galacturonic acid to galactaric acid.

22. The host strain of claim 21, wherein the nucleotide sequence is obtained from *Agrobacterium* species.

23. The host strain of claim 22, wherein the strain belongs to genera *Aspergillus* or *Hypocrea*.

* * * * *

SEQUENCE LISTING

```
<160> NUMBER OF SEQ ID NOS: 20

<210> SEQ ID NO 1
<211> LENGTH: 30
<212> TYPE: DNA
<213> ORGANISM: Artificial
<220> FEATURE:
<223> OTHER INFORMATION: synthesized sequence
<220> FEATURE:
<221> NAME/KEY: misc_feature
<222> LOCATION: (1)..(30)
<223> OTHER INFORMATION: primer

<400> SEQUENCE: 1
cacagcaaag acgcagaatt cgcttggaag                                      30

<210> SEQ ID NO 2
<211> LENGTH: 29
<212> TYPE: DNA
<213> ORGANISM: Artificial
<220> FEATURE:
<223> OTHER INFORMATION: synthesized sequence
<220> FEATURE:
<221> NAME/KEY: misc_feature
<222> LOCATION: (1)..(29)
<223> OTHER INFORMATION: primer

<400> SEQUENCE: 2
ggcttgggat cccgctgatc attcagctc                                       29

<210> SEQ ID NO 3
<211> LENGTH: 801
```

```
<212> TYPE: DNA
<213> ORGANISM: Agrobacterium tumefaciens

<400> SEQUENCE: 3
atggcgatga acggcttct tgttaccggt gcggcgggcc agcttggccg cgtcatgcgc    60
gagcgtctcg caccgatggc ggagatactg cgccttgccg atctctcccc gctcgacccg   120
gcagggccga acgaagaatg cgtgcaatgc gaccttgccg atgccaatgc cgtgaatgcc   180
atggtcgccg gttgcgacgg tattgttcat ctcggcggca tctcggtgga aaagcccttc   240
gaacaaatcc ttcagggcaa tatcatcggg ctttataatc tctacgaggc cgcccgcgcc   300
catggacagc cacgcatcgt ctttgccagc tccaaccaca cgatcggcta ttatccgcag   360
accgaacggc tcggtccgga tgttccggcg cggccggacg tctttacgg cgtctccaaa    420
tgtttcggcg aaaacctcgc cgcatgtat ttcgataaat cgggcagga cggcgctg      480
gtgcgcatcg gctcctgtac gccggaaccc aacaattacc gcatgctgtc cacctggttt   540
tcgcacgatg atttcgtgtc gctgatcgag gcggtgtttc gcgcgccggt gctcggctgc   600
ccggtcgtct ggggggcatc ggccaatgat gcgggctggt gggacaattc gcatcttggc   660
tttctgggct ggaaaccgaa ggataatgcc gaggccttcc ggcggcatat aaccgagacg   720
acaccgccac cggacccgaa tgacgcgttg gtgcggttcc agggcggtac gtttgtcgac   780
aacccgatct tcaaacagag c                                             801

<210> SEQ ID NO 4
<211> LENGTH: 267
<212> TYPE: PRT
<213> ORGANISM: Agrobacterium tumefaciens

<400> SEQUENCE: 4

Met Ala Met Lys Arg Leu Leu Val Thr Gly Ala Ala Gly Gln Leu Gly
1               5                   10                  15

Arg Val Met Arg Glu Arg Leu Ala Pro Met Ala Glu Ile Leu Arg Leu
            20                  25                  30

Ala Asp Leu Ser Pro Leu Asp Pro Ala Gly Pro Asn Glu Glu Cys Val
        35                  40                  45

Gln Cys Asp Leu Ala Asp Ala Asn Ala Val Asn Ala Met Val Ala Gly
    50                  55                  60

Cys Asp Gly Ile Val His Leu Gly Gly Ile Ser Val Glu Lys Pro Phe
65                  70                  75                  80

Glu Gln Ile Leu Gln Gly Asn Ile Ile Gly Leu Tyr Asn Leu Tyr Glu
                85                  90                  95

Ala Ala Arg Ala His Gly Gln Pro Arg Ile Val Phe Ala Ser Ser Asn
            100                 105                 110

His Thr Ile Gly Tyr Tyr Pro Gln Thr Glu Arg Leu Gly Pro Asp Val
        115                 120                 125

Pro Ala Arg Pro Asp Gly Leu Tyr Gly Val Ser Lys Cys Phe Gly Glu
    130                 135                 140

Asn Leu Ala Arg Met Tyr Phe Asp Lys Phe Gly Gln Glu Thr Ala Leu
145                 150                 155                 160

Val Arg Ile Gly Ser Cys Thr Pro Glu Pro Asn Asn Tyr Arg Met Leu
                165                 170                 175

Ser Thr Trp Phe Ser His Asp Asp Phe Val Ser Leu Ile Glu Ala Val
            180                 185                 190

Phe Arg Ala Pro Val Leu Gly Cys Pro Val Val Trp Gly Ala Ser Ala
        195                 200                 205
```

```
Asn Asp Ala Gly Trp Trp Asp Asn Ser His Leu Gly Phe Leu Gly Trp
            210                 215                 220

Lys Pro Lys Asp Asn Ala Glu Ala Phe Arg Arg His Ile Thr Glu Thr
225                 230                 235                 240

Thr Pro Pro Pro Asp Pro Asn Asp Ala Leu Val Arg Phe Gln Gly Gly
                245                 250                 255

Thr Phe Val Asp Asn Pro Ile Phe Lys Gln Ser
            260                 265

<210> SEQ ID NO 5
<211> LENGTH: 55
<212> TYPE: DNA
<213> ORGANISM: Artificial
<220> FEATURE:
<223> OTHER INFORMATION: synthesized sequence
<220> FEATURE:
<221> NAME/KEY: misc_feature
<222> LOCATION: (1)..(55)
<223> OTHER INFORMATION: primer

<400> SEQUENCE: 5
ccggaattca ccatgcacca ccatcaccat cacatggcga tgaaacggct tcttg         55

<210> SEQ ID NO 6
<211> LENGTH: 29
<212> TYPE: DNA
<213> ORGANISM: Artificial
<220> FEATURE:
<223> OTHER INFORMATION: synthesized sequence
<220> FEATURE:
<221> NAME/KEY: misc_feature
<222> LOCATION: (1)..(29)
<223> OTHER INFORMATION: primer

<400> SEQUENCE: 6
ggcttgggat cccgctgatc attcagctc                                      29

<210> SEQ ID NO 7
<211> LENGTH: 53
<212> TYPE: DNA
<213> ORGANISM: Artificial
<220> FEATURE:
<223> OTHER INFORMATION: synthesized sequence
<220> FEATURE:
<221> NAME/KEY: misc_feature
<222> LOCATION: (1)..(53)
<223> OTHER INFORMATION: primer

<400> SEQUENCE: 7
gtaacgccag ggttttccca gtcacgacga agcttatatc caccgtgtcc cag           53

<210> SEQ ID NO 8
<211> LENGTH: 49
<212> TYPE: DNA
<213> ORGANISM: Artificial
<220> FEATURE:
<223> OTHER INFORMATION: synthesized sequence
<220> FEATURE:
<221> NAME/KEY: misc_feature
<222> LOCATION: (1)..(49)
<223> OTHER INFORMATION: primer

<400> SEQUENCE: 8
atccacttaa cgttactgaa atctccaacg acgcagttgt ttgagcaac                49

<210> SEQ ID NO 9
```

```
<211> LENGTH: 49
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(49)
<223> OTHER INFORMATION: primer

<400> SEQUENCE: 9
ctccttcaat atcatcttct gtctccgact tgcattggtc agagcggta          49

<210> SEQ ID NO 10
<211> LENGTH: 55
<212> TYPE: DNA
<213> ORGANISM: Artificial
<220> FEATURE:
<223> OTHER INFORMATION: synthesized sequence
<220> FEATURE:
<221> NAME/KEY: misc_feature
<222> LOCATION: (1)..(55)
<223> OTHER INFORMATION: primer

<400> SEQUENCE: 10
gcggataaca atttcacaca ggaaacagca agcttaagca gtggatgact tgctg    55

<210> SEQ ID NO 11
<211> LENGTH: 30
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(30)
<223> OTHER INFORMATION: primer

<400> SEQUENCE: 11
gtcggagaca gaagatgata ttgaaggagc                                30

<210> SEQ ID NO 12
<211> LENGTH: 28
<212> TYPE: DNA
<213> ORGANISM: Artificial
<220> FEATURE:
<223> OTHER INFORMATION: synthesized sequence
<220> FEATURE:
<221> NAME/KEY: misc_feature
<222> LOCATION: (1)..(28)
<223> OTHER INFORMATION: primer

<400> SEQUENCE: 12
gttggagatt tcagtaacgt taagtgga                                  28

<210> SEQ ID NO 13
<211> LENGTH: 31
<212> TYPE: DNA
<213> ORGANISM: Artificial
<220> FEATURE:
<223> OTHER INFORMATION: synthesized sequence
<220> FEATURE:
<221> NAME/KEY: misc_feature
<222> LOCATION: (1)..(31)
<223> OTHER INFORMATION: primer

<400> SEQUENCE: 13
tatactcgag tgaattgcac tcttcgtacc g                              31
```

```
<210> SEQ ID NO 14
<211> LENGTH: 31
<212> TYPE: DNA
<213> ORGANISM: Artificial
<220> FEATURE:
<223> OTHER INFORMATION: synthesized sequence
<220> FEATURE:
<221> NAME/KEY: misc_feature
<222> LOCATION: (1)..(31)
<223> OTHER INFORMATION: primer

<400> SEQUENCE: 14
tataccatgg tgtgattgct gtggtgtaaa t                              31

<210> SEQ ID NO 15
<211> LENGTH: 32
<212> TYPE: DNA
<213> ORGANISM: Artificial
<220> FEATURE:
<223> OTHER INFORMATION: synthesized sequence
<220> FEATURE:
<221> NAME/KEY: misc_feature
<222> LOCATION: (1)..(32)
<223> OTHER INFORMATION: primer

<400> SEQUENCE: 15
tataccatgg ccgtttatga ttctggtcca tc                             32

<210> SEQ ID NO 16
<211> LENGTH: 30
<212> TYPE: DNA
<213> ORGANISM: Artificial
<220> FEATURE:
<223> OTHER INFORMATION: synthesized sequence
<220> FEATURE:
<221> NAME/KEY: misc_feature
<222> LOCATION: (1)..(30)
<223> OTHER INFORMATION: primer

<400> SEQUENCE: 16
tatagaattc tcgagttaat tcccttagcg                                30

<210> SEQ ID NO 17
<211> LENGTH: 30
<212> TYPE: DNA
<213> ORGANISM: Artificial
<220> FEATURE:
<223> OTHER INFORMATION: synthesized sequence
<220> FEATURE:
<221> NAME/KEY: misc_feature
<222> LOCATION: (1)..(30)
<223> OTHER INFORMATION: primer

<400> SEQUENCE: 17
tatacccggg tgattgaggt gattggcgat                                30

<210> SEQ ID NO 18
<211> LENGTH: 28
<212> TYPE: DNA
<213> ORGANISM: Artificial
<220> FEATURE:
<223> OTHER INFORMATION: synthesized sequence
<220> FEATURE:
<221> NAME/KEY: misc_feature
<222> LOCATION: (1)..(28)
<223> OTHER INFORMATION: primer

<400> SEQUENCE: 18
tatacccggg ttatcacgcg acggacat                                  28
```

<210> SEQ ID NO 19
<211> LENGTH: 901
<212> TYPE: DNA
<213> ORGANISM: Pseudomonas sp.

<400> SEQUENCE: 19

```
caaggcctag gcgcgccatg agctcggatc cgggcccatg gcctccgccc acaccaccca      60
gaccccttc aaccgcctcc tcctcaccgg cgctgctggc ggcctcggca aggtcctccg      120
cgaaaccctc cgcccctact cccacatcct ccgcctctcc gatatcgccg agatggcccc      180
tgccgtcggc gatcacgagg aagtccaggt ctgcgatctc gccgataagg atgccgtcca      240
ccgcctcgtc gagggcgtcg atgccatcct ccacttcggc ggtgttagcg tcgagcgccc      300
cttcgaggaa atcctcggcg ccaacatctg cggcgtgttc cacatctacg aggccgctcg      360
ccgtcatggt gtcaagcgcg tcatcttcgc ctccagcaac cacgtcatcg gcttctacaa      420
gcagaacgaa accatcgatg cccactcccc acgccgccct gattcctact acggcctctc      480
caagtcctac ggcgaggata tggcctcctt ctacttcgat cgctacggca tcgaaaccgt      540
gtccatccgc atcggctcca gcttccccga gccccagaac cgccgcatga tgtccacctg      600
gctgtccttc gatgatctca cccgcctgct cgagcgcgcc ctctacaccc ccgatgtcgg      660
ccacaccgtc gtctacggcg tgtccgataa caagaccgtc tggtgggata accgattcgc      720
ttctaagctc gattacgccc ccaaggattc ctccgaggtg ttccgcgcca aggtggacgc      780
tcagcccatg cctgctgatg atgatcctgc tatggtctac cagggtggtg ccttcgtcgc      840
ctccggcccc ttcggcgata agtaaactag tggatccggt acctcttaat taactggcct      900
c                                                                     901
```

<210> SEQ ID NO 20
<211> LENGTH: 275
<212> TYPE: PRT
<213> ORGANISM: Pseudomonas sp.

<400> SEQUENCE: 20

```
Met Ala Ser Ala His Thr Thr Gln Thr Pro Phe Asn Arg Leu Leu Leu
1               5                   10                  15

Thr Gly Ala Ala Gly Gly Leu Gly Lys Val Leu Arg Glu Thr Leu Arg
            20                  25                  30

Pro Tyr Ser His Ile Leu Arg Leu Ser Asp Ile Ala Glu Met Ala Pro
        35                  40                  45

Ala Val Gly Asp His Glu Glu Val Gln Val Cys Asp Leu Ala Asp Lys
    50                  55                  60

Asp Ala Val His Arg Leu Val Glu Gly Val Asp Ala Ile Leu His Phe
65                  70                  75                  80

Gly Gly Val Ser Val Glu Arg Pro Phe Glu Glu Ile Leu Gly Ala Asn
                85                  90                  95

Ile Cys Gly Val Phe His Ile Tyr Glu Ala Ala Arg Arg His Gly Val
            100                 105                 110

Lys Arg Val Ile Phe Ala Ser Ser Asn His Val Ile Gly Phe Tyr Lys
        115                 120                 125

Gln Asn Glu Thr Ile Asp Ala His Ser Pro Arg Arg Pro Asp Ser Tyr
    130                 135                 140

Tyr Gly Leu Ser Lys Ser Tyr Gly Glu Asp Met Ala Ser Phe Tyr Phe
145                 150                 155                 160

Asp Arg Tyr Gly Ile Glu Thr Val Ser Ile Arg Ile Gly Ser Ser Phe
```

-continued

```
                    165                 170                 175
Pro Glu Pro Gln Asn Arg Arg Met Met Ser Thr Trp Leu Ser Phe Asp
            180                 185                 190

Asp Leu Thr Arg Leu Leu Glu Arg Ala Leu Tyr Thr Pro Asp Val Gly
        195             200             205

His Thr Val Val Tyr Gly Val Ser Asp Asn Lys Thr Val Trp Trp Asp
    210             215             220

Asn Arg Phe Ala Ser Lys Leu Asp Tyr Ala Pro Lys Asp Ser Ser Glu
225             230             235             240

Val Phe Arg Ala Lys Val Asp Ala Gln Pro Met Pro Ala Asp Asp Asp
                245             250             255

Pro Ala Met Val Tyr Gln Gly Gly Ala Phe Val Ala Ser Gly Pro Phe
            260             265             270

Gly Asp Lys
        275
```